United States Patent [19]
Mais et al.

[11] Patent Number: 5,157,170
[45] Date of Patent: Oct. 20, 1992

[54] PROCESS FOR REACTING POLYHALOGENATED AROMATIC COMPOUNDS WITH MONOHALOGENATED OR NONHALOGENATED AROMATIC COMPOUNDS

[75] Inventors: Franz-Josef Mais, Düsseldorf; Helmut Fiege, Leverkusen, both of Fed. Rep. of Germany

[73] Assignee: Bayer Aktiengesellschaft, Leverkusen, Fed. Rep. of Germany

[21] Appl. No.: 805,433

[22] Filed: Dec. 11, 1991

[30] Foreign Application Priority Data

Jan. 19, 1991 [DE] Fed. Rep. of Germany ....... 4101528

[51] Int. Cl.$^5$ .................. C07C 22/13; C07C 22/00
[52] U.S. Cl. .................. 570/147; 570/204; 570/206; 570/208; 570/210
[58] Field of Search ............... 570/147, 208, 204, 163, 570/260, 206, 210

[56] References Cited

U.S. PATENT DOCUMENTS

| | | | |
|---|---|---|---|
| 3,852,365 | 12/1974 | Mahler | 570/147 |
| 4,808,759 | 2/1989 | Paparatto | 570/204 |
| 4,822,929 | 4/1989 | Paparatto | 570/204 |

FOREIGN PATENT DOCUMENTS

| | | | |
|---|---|---|---|
| 699234 | 12/1964 | Canada | 570/163 |
| 2120328 | 6/1987 | Japan | 570/204 |
| 2120329 | 6/1987 | Japan | 570/204 |
| 982625 | 2/1965 | United Kingdom | 570/163 |

Primary Examiner—Alan Siegel
Attorney, Agent, or Firm—Sprung Horn Kramer & Woods

[57] ABSTRACT

The halogen of a polyhalogenated aromatic compound can be transferred to a monohalogenated or nonhalogenated aromatic compound by reaction in the presence of ruthenium as the element or in the form of compounds and if desired with one or more metal compounds from subgroups I and II of the Periodic Table.

11 Claims, No Drawings

PROCESS FOR REACTING POLYHALOGENATED AROMATIC COMPOUNDS WITH MONOHALOGENATED OR NONHALOGENATED AROMATIC COMPOUNDS

The present invention relates to a method in which polyhalogenated aromatic compounds are reacted with monohalogenated or nonhalogenated aromatic compounds with the purpose of transferring the halogen of the polyhalogenated aromatic compound to the monohalogenated or nonhalogenated aromatic compound and simultaneously transferring the hydrogen atoms of the monohalogenated or nonhalogenated aromatic compound to the polyhalogenated aromatic compound.

The reaction of polychlorinated aromatic compounds such as 1,2-dichlorobenzene or 1,2,4-trichlorobenzene with benzene is known from Japanese Application JP-01 311-032. As catalyst, activated charcoal charged with palladium chloride ($PdCl_2$) and a rare earth metal chloride such as $CeCl_3$ is used. In general this reaction results in mixtures of the two starting materials such as 1,2-dichlorobenzene and benzene with the product of the chlorine transfers, chlorobenzene, together with the isomerisation products of the polychlorinated starting material, 1,3- and 1,4-dichlorobenzene.

The general chemical literature (Chem. Lett. 1987, 2051) also discloses the reaction of 1,2-dichlorobenzene with benzene in the presence of altivated charcoal charged with chlorides of iridium, rhodium or osmium. However, these catalysts show significantly poorer activity in chlorine transfer than activated charcoals charged with palladium chloride/rare earth chloride.

In addition, EP 256 479 discloses the reaction of polyiodobenzene such as 1,4-diiodobenzene with benzene. As catalysts, type X or Y zeolites are used, which can be interchanged with thallium or rare earth metals. The reaction product is a mixture of the benzene used in excess and iodobenzene.

A process has now been found for reacting polyhalogenated aromatic compounds with monohalogenated or nonhalogenated aromatic compounds, in which the halogen of the polyhalogenated aromatic compounds is transferred to the monohalogenated or nonhalogenated aromatic compounds and the hydrogen of the monohalogenated or nonhalogenated aromatic compounds is simultaneously transferred to the polyhalogenated aromatic compounds in the presence of a catalyst, characterised in that a catalyst is used which contains ruthenium as the element or in the form of compounds and if desired one or more metals or compounds of metals from subgroups I and II of the Periodic Table.

According to the invention, the polyhalogenated aromatic compounds used can be polyhalogenated benzenes, polyhalogenated naphthalenes or polyhalogenated biphenyls. These polyhalogenated starting materials have, according to the invention, at least 2 halogen atoms when nonhalogenated aromatic compounds are used and at least 3 halogen atoms when monohalogenated aromatic compounds are used, up to the particular maximum saturation, i.e. 2–6 halogen atoms in the benzene system, 2–8 halogen atoms in the naphthalene system and 2–10 halogen atoms in the biphenyl system.

According to the invention, the halogen used in the polyhalogenated starting materials can be chlorine, bromine or iodine, preferably chlorine or bromine, very especially preferably chlorine.

The polyhalogenated aromatic compounds can be polysubstituted by a single halogen. However, it is also possible for the polyhalogenated aromatic compound to be polysubstituted by two or three different halogens. According to the invention aromatic compounds are, however, preferably polysubstituted by a single halogen.

As examples of polyhalogenated aromatic compounds that can be used according to the invention the following can be mentioned, without, however, restricting the invention to these:

1,2-dichlorobenzene,
1,3-dichlorobenzene,
1,4-dichlorobenzene,
1,2,4-trichlorobenzene,
1,2,3-trichlorobenzene,
1,3,5-trichlorobenzene,
1,2,3,4-tetrachlorobenzene,
1,2,4,5-tetrachlorobenzene,
pentachlorobenzene,
hexachlorobenzene,
positionally isomeric dibromobenzenes,
positionally isomeric tribromobenzenes,
positionally isomeric tetrabromobenzenes,
positionally isomeric diiodobenzenes,
positionally isomeric dichloronaphthalenes,
positionally isomeric tri- and tetrachloronaphthalenes,
positionally isomeric di-, tri- and tetrachlorobiphenyls,
positionally isomeric di-, tri- and tetrabromobiphenyls.

According to the invention it is preferred to use mixtures of the polyhalogenated aromatic compounds; examples which can be named are:

A mixture of variable proportions of tri- and tetrachlorobenzenes with smaller proportions of penta- and hexachlorobenzene.

A mixture of chlorinated naphthalenes with an average degree of chlorination of for example 4–6.

A mixture of chlorinated biphenyls with a degree of chlorination of for example 3–6.

In addition, according to the invention it is also possible to use mixtures of polyhalogenated benzenes and polyhalogenated naphthalenes, or of polyhalogenated benzenes and polyhalogenated biphenyls etc., but this is not preferred.

The monohalogenated or nonhalogenated aromatic compounds used according to the invention may be halogenobenzene or benzene. The halogen used according to the invention in the monohalogenated aromatic compound may be fluorine, chlorine, bromine or iodine. The nonhalogenated aromatic compound used according to the invention is preferably benzene.

The ratio of the polyhalogenated aromatic compounds to the monohalogenated or nonhalogenated aromatic compounds used is in the context of the present invention in principle unrestricted. In the interest of practical exploitation, however, there is little point in using the monohalogenated aromatic compound in a molar deficit. It is therefore preferred according to the invention to use the monohalogenated or nonhalogenated aromatic compound in a molar excess.

The catalysts usable according to the invention contain ruthenium as the element or in the form of compounds. To carry out a continuous industrial process it is necessary to convert the ruthenium or its compounds into a convenient form. It is therefore preferred according to the invention to apply ruthenium or its compounds to a support material. It is further preferred according to the invention that this support material is an activated charcoal, which may be granulated.

The preparation of the ruthenium-charged activated charcoal can for example be achieved by impregnating, with for example an aqueous ruthenium salt solution, for example a granulated activated charcoal, which is then dried. The dry catalysts charged with ruthenium compounds thus obtained can then if desired be further modified by washing with further solutions, e.g. aqueous common salt solution, aqueous ammonia solution, aqueous hydrazine solution, dilute aqueous acid etc.

It is further possible to impregnate the thus-charged catalysts again with for example an aqueous metal solution and to dry them again. In this manner a catalyst is obtained which contains in addition to the ruthenium salt one or more salts of further so-called co-metal salts. According to the invention it is very especially preferable to use catalysts of activated charcoal charged with ruthenium salts and one or more co-metal salts.

The ruthenium salt used may be all simple soluble ruthenium salts, for example the halides, particularly preferably ruthenium chloride. The co-metal salts used according to the invention may be salts of elements of sub-groups I and II, i.e., for example, copper, silver, gold, zinc, mercury or cadmium, very particularly preferably salts of copper and silver.

The molar ratio of ruthenium salt to co-metal salt or to the sum of the co-metal salts can be varied within the range 1:10 to 10:1; a molar ratio range of 2:1 to 1:2 is preferred.

The process according to the invention is carried out in the gaseous phase, where the solid heterogeneous catalyst can be present in a technically normal arrangement e.g. as a solid bed or fluidised bed.

In addition to the gaseous or vapour form starting materials and their gaseous or vapour form reaction products another gas or vapour inert under the reaction conditions can be present in the reaction chamber for dilution. Examples which may be mentioned without representing a restriction are: nitrogen, argon or steam.

The process according to the invention can be carried out at standard pressure, reduced pressure or increased pressure, preferably standard pressure or increased pressure.

The reaction temperatures according to the invention are variable within a wide range. The lower limit of reaction temperature is restricted in that at the reaction pressure selected all the starting materials and their reaction products should be present in the gaseous phase. The upper temperature limit is restricted in that at too high a temperature side reactions, for example degradation reactions of the aromatic compound or polymerisations can occur, which can thus lead to the deactivation of the catalyst. In general according to the invention the reaction temperature is selected in the range 200°-600° C., preferably the range 300°-500° C.

An illustrative embodiment of the process according to the invention is, for example, the following, without limiting the invention to this embodiment:

A catalyst is produced, for example, from a wood charcoal-based, steam-activated, very well-washed granular activated charcoal, which contains 5 g of ruthenium per liter as ruthenium chloride. After drying, this catalyst is impregnated with a co-metal salt solution (e.g.: $CuCl_2$ solution or $AgNO_3$ solution) and dried again. The catalyst, which now contains the two salts in a molar ratio of for example 1:1, is placed in a reaction tube having a ratio of the diameter of the reaction tube to the diameter of the catalyst granules of 20:1 to 50:1. The catalyst is then heated for 2 h at the desired temperature, e.g. 400° C., under a gentle stream of inert gas, e.g. nitrogen. Following this, a mixture of a polyhalogenated aromatic compound with a monohalogenated or nonhalogenated aromatic compound, e.g. isomeric trichlorobenzenes with benzene, in the gaseous phase from a pre-evaporation zone and a pre-heating zone is passed over the catalyst, pre-heated to the desired temperature of 400° C. In addition if desired an inert gas, e.g. nitrogen, can be blown in. The gaseous product mixture is passed through a short post-heating zone and condensed in a chilled product trap.

The process according to the invention allows the transfer of the halogen from a polyhalogenated aromatic compound to a monohalogenated or non-halogenated aromatic compound in the presence of ruthenium-containing catalysts. That these particular ruthenium-containing catalysts show good activity in halogen transfer must be considered extremely surprising according to the state of the art. Until now only activated charcoals charged with, inter alia, palladium chloride were known for a similar chlorine transfer. From the general chemical literature (Chem. Lett. 1987, 2051; Chem. Lett. 1989, 1265) it can moreover be inferred that other noble metal chlorides are without activity or have weak activity.

It is moreover extremely surprising that a marked increase in activity of the ruthenium-containing catalysts occurs as a result of the presence of additional co-metals of subgroups I and II of the Periodic Table, e.g. copper or silver compounds. This fact is not deducible from known chemical knowledge.

The possibility created according to the invention for transferring the halogen from, for example, a polychlorinated aromatic compound to, for example, a non-halogenated is extremely valuable for example for the disposal of highly chlorinated waste isomer mixtures from benzene chlorination or for example for dehalogenation and thus disposal of polyhalogenated naphthalenes or biphenyl mixtures. At the same time, during the dechlorination of polychlorinated benzenes, chlorobenzene and possibly dichlorobenzenes may additionally be obtained as valuable products by reaction with benzene.

The following examples are intended to clarify the process according to the invention, without however restricting it to these examples:

EXAMPLES

Example 1
Preparation of a catalyst (Ru/Cu-1)

1 liter of a dry, wood charcoal-based, well-washed, steam-activated granular activated charcoal (granule size 1-3 mm diameter, bulk density about 400 g/l) was impregnated with a sufficient quantity of a commercially available aqueous ruthenium chloride solution, containing mainly ruthenium of oxidation state +3, so that the catalyst after drying at 100° C. in vacuo contained 5.00 g of ruthenium per liter as the chloride. The dry catalyst was impregnated with a solution of 8.40 g of $CuCl_2.2H_2O$ in 170 ml of water and dried again at 100° C. in vacuo. The dry catalyst then contained 5.00 g of Ru/l and 3.14 g of Cu/l mainly as chlorides. The molar ratio of the elements ruthenium and copper was 1:1. The bulk density of the dry catalyst was about 420 g/l.

Example 2

Preparation of a catalyst (Ru/Cu-2)

The process of Example 1 was repeated, except that instead of a wood charcoal-based granular activated charcoal, a peat-based well-washed steam-activated dry shaped activated charcoal (extrudates, length: 2–5 mm, diameter: about 0.8 mm, bulk density: about 390 g/l) was used. The finished dry catalyst contained 5.00 g of Ru/l and 3.14 g of Cu/l, corresponding to a molar ratio of both elements of approximately 1:1. The bulk density of the dry catalyst was about 410 g/l.

Example 3

Preparation of a catalyst (Ru/Ag-1)

1 liter of the granular activated charcoal of Example 1 was, as described therein, impregnated with a sufficient quantity of ruthenium chloride solution and dried so that 5.00 g of Ru/l resulted. This dry catalyst was impregnated with a solution of 8.40 g of $AgNO_3$ in 180 ml of water and again dried at 100° C. in vacuo. This dry catalyst was then washed with 3.30 l of a 1% aqueous common salt solution and again dried at 100° C. in vacuo. It then contained 5.00 g of Ru/l and 5.34 of Ag/l. That corresponded to a molar ratio of ruthenium to silver of approximately 1:1. The bulk density of the dry catalyst was about 420 g/l.

Example 4

Production of a catalyst (Ru/Ag-2) The process of Example 3 was repeated, except that instead of the activated charcoal described therein, the peat-based shaped charcoal described in Example 2 was used. The dry finished catalyst then contained 5.00 g of Ru/l and 5.34 g of Ag/l, corresponding to a molar ratio of the two elements of approximately 1:1. The bulk density of the dry catalyst was about 419 g/l.

Examples 5 to 8

A vertical reaction tube was in each case packed with 150 ml of the catalysts described in Examples 1 to 4. A fixed catalyst bed of about 21 cm in height was obtained, which was heated externally. The catalyst bed was first heated at 400° C. for 2 hours under a nitrogen stream of 20 l/h. Then, at a rate of 15.0 g/h a mixture of 13.5 g of 1,2,4-trichlorobenzene and 76.5 g benzene in the gaseous phase from a pre-evaporator, and preheated to 400° C., was passed over the catalyst bed at 400° C. At the same time, in addition, nitrogen was slowly introduced at a rate of 5–7 l/h. After the end of the addition, i.e. after 6 h, there was a further post-heating phase of 1 h under a nitrogen stream of 5–7 l/h. The effluent gases were condensed in a cold trap. After two, four and seven hours these cold traps were changed and the condensate was analysed with a calibrated GC method, so that the GC % figures correspond to weight percent. The results of the four trials are to be found in Tables 1–4.

Comparison example 9

(Catalyst according to JP-01/311-032)

The shaped activated charcoal described in Example 2 was, as described in Example 1, impregnated with a sufficient quantity of a commercially available aqueous solution of $PdCl_2$ so that the catalyst after drying contained 5.00 g of Pd/l. The dry catalyst was then impregnated with a solution of 17.53 g of $CeCl_3.7H_2O$ in 170 ml of water and dried at 100° C. in vacuo. The bulk density after this was about 425 g/l. This catalyst was then, as described in Examples 5–8, heated for 2 h at 400° C. under nitrogen. Then analogously to Examples 5–8 13.5 g of 1,2,4-trichlorobenzene and 76.5 g of benzene were passed through the fixed bed. The condensate was trapped and analysed analogously to Examples 5–8. The result is likewise to be found in Tables 1–4.

TABLE 1

Trial conditions of Examples 5–8 and the Comparison Example 9.
Result of Examples 5–8 and the comparison Example 9 in Tables 1–4

| Example | Catalyst | Catalyst amount | Starting materials | Flow time | Post-heating time | Temperature |
|---|---|---|---|---|---|---|
| 5 | Ru/Cu-1 from Example 1 | 150 ml | 13.5 g 1,2,4-trichlorobenzene + 76.5 g benzene | 6 h | 1 h | 400° C. |
| 6 | Ru/Cu-2 from Example 2 | 150 ml | 13.5 g 1,2,4-trichlorobenzene + 76.5 g benzene | 6 h | 1 h | 400° C. |
| 7 | Ru/Ag-1 from Example 3 | 150 ml | 13.5 g 1,2,4-trichlorobenzene + 76.5 g benzene | 6 h | 1 h | 400° C. |
| 8 | Ru/Ag-2 from Example 4 | 150 ml | 13.5 g 1,2,4-trichlorobenzene + 76.5 g benzene | 6 h | 1 h | 400° C. |
| Comparison Example 9 | Pd/Ce | 150 ml | 13.5 g 1,2,4-trichlorobenzene + 76.5 g benzene | 6 h | 1 h | 400° C. |

TABLE 2

Composition and weight of the condensate of Examples 5–8 and of the Comparison Example 9 for the trial period 0–2 h.

| Example | Benzene | Chlorobenzene | 1,2-Dichlorobenzene | 1,3 Dichlorobenzene | 1,4-Dichlorobenzene | 1,2,3-Trichlorobenzene | 1,2,4-Trichlorobenzene | Weight g | Weight as % of initial |
|---|---|---|---|---|---|---|---|---|---|
| 5 | 89.49% | 10.50% | — | 0.15% | — | — | — | 27.83 | 92.77 |
| 6 | 90.50% | 9.50% | — | — | — | — | — | 26.97 | 89.90 |
| 7 | 87.88% | 12.12% | — | — | — | — | — | 26.13 | 87.10 |
| 8 | 88.42% | 11.58% | — | — | — | — | — | 26.30 | 87.66 |
| Comparison Example 9 | 90.19% | 9.38% | 0.08% | 0.27% | 0.08% | — | — | 25.90 | 86.33 |

TABLE 3

Composition and weight of the condensate of Examples 5-8 and of the Comparison Example 9 for the trial period 2-4 h.

| Example | Benzene | Chlorobenzene | 1,2-Dichlorobenzene | 1,3 Dichlorobenzene | 1,4-Dichlorobenzene | 1,2,3-Trichlorobenzene | 1,2,4-Trichlorobenzene | Weight g | Weight as % of initial |
|---|---|---|---|---|---|---|---|---|---|
| 5 | 90.89% | 9.11% | — | — | — | — | — | 26.93 | 89.78 |
| 6 | 90.96% | 9.04% | — | — | — | — | — | 25.87 | 86.23 |
| 7 | 86.31% | 13.12% | 0.47% | 0.10% | — | — | — | 29.03 | 96.78 |
| 8 | 86.48% | 12.99% | 0.37% | 0.13% | 0.03% | — | — | 28.30 | 94.33 |
| Comparison Example 9 | 87.78% | 8.47% | 1.05% | 1.20% | 1.09% | — | — | 27.50 | 91.67 |

TABLE 4

Composition and weight of the condensate of Examples 5-8 and of the Comparison Example 9 for the trial period 4-7 h (end of the post-run time).

| Example | Benzene | Chlorobenzene | 1,2-Dichlorobenzene | 1,3 Dichlorobenzene | 1,4-Dichlorobenzene | 1,2,3-Trichlorobenzene | 1,2,4-Trichlorobenzene | Weight g | Weight as % of initial |
|---|---|---|---|---|---|---|---|---|---|
| 5 | 89.75% | 9.17% | 0.19% | 0.50% | 0.39% | — | — | 28.03 | 93.44 |
| 6 | 90.69% | 8.00% | 0.10% | 0.70% | 0.51% | — | — | 28.37 | 94.57 |
| 7 | 85.48% | 11.01% | 2.56% | 0.48% | 0.47% | — | — | 29.63 | 98.78 |
| 8 | 87.16% | 8.51% | 2.51% | 0.82% | 0.71% | — | 0.29% | 29.50 | 98.33 |
| Comparison Example 9 | 86.47% | 5.78% | 1.65% | 2.61% | 1.68% | — | 1.81% | 29.60 | 98.67 |

Example 10

The process of Example 8 was repeated, except that instead of the mixture there of 13.5 g of 1,2,4-trichlorobenzene and 76.5 g of benzene, here a mixture of 16.4 g of 1,2-dichlorobenzene and 73.6 g of benzene was used. The result is to be found in Tables 5-8.

Example 11

The process of Example 8 was repeated, except that instead of the mixture there of 13.5 g of 1,2,4-trichlorobenzene and 76.5 g of benzene, here a mixture of 6.57 g of 1,2,4,5-tetrachlorobenzene and 83.43 g of benzene was passed over the catalyst. The result is to be found in Tables 5-8.

Example 12

The process of Example 8 was repeated, except that instead of the mixture used there a mixture of 3.87 g of hexachlorobenzene and 86.13 g of benzene was used. The result is likewise to be found in Tables 5-8.

Example 13

The process of Example 8 was repeated, except that instead of the mixture used there a mixture of 9.81 g of 1,2,4-trichlorobenzene and 80.19 g of chlorobenzene was used. The result of the trial is to be found in Tables 5-8.

TABLE 5

Trial conditions of Examples 10-13.
Result of Trials 10-13 in Tables 5-8

| Example | Catalyst | Catalyst amount | Starting materials | Flow time | Post-heating time | Temperature |
|---|---|---|---|---|---|---|
| 10 | Ru/Ag-2 from Example 4 | 150 ml | 16.4 g 1,2-dichlorobenzene + 73.6 g benzene | 6 h | 1 h | 400° C. |
| 11 | Ru/Ag-2 from Example 4 | 150 ml | 6.57 g 1,2,4,5-tetrachlorobenzene + 83.43 g benzene | 6 h | 1 h | 400° C. |
| 12 | Ru/Ag-2 from Example 4 | 150 ml | 3.87 g hexachlorobenzene + 86.13 g benzene | 6 h | 1 h | 400° C. |
| 13 | Ru/Ag-2 from Example 4 | 150 ml | 9.81 g 1,2,4-trichlorobenzene + 80.19 g chlorobenzene | 6 h | 1 h | 400° C. |

TABLE 6

Composition and weight of the condensate of Examples 10-13 for the trial period 0-2 h.

| Example | Benzene | Chlorobenzene | 1,2-Dichlorobenzene | 1,3 Dichlorobenzene | 1,4-Dichlorobenzene | 1,2,3-Trichlorobenzene | 1,2,4-Trichlorobenzene | Weight g | Weight as % of initial |
|---|---|---|---|---|---|---|---|---|---|
| 10 | 86.30% | 13.61% | 0.09% | — | — | — | — | 27.13 | 90.43 |
| 11 | 93.99% | 6.01% | — | — | — | — | — | 27.30 | 91.00 |
| 12 | 93.68% | 6.32% | — | — | — | — | — | 27.20 | 90.67 |
| 13 | 6.36% | 70.96% | 2.36% | 14.03% | 5.73% | 0.12% | 0.44% | 21.60 | 72.00 |

TABLE 7

Composition and weight of the condensate of Examples 10-13 for the trial period 2-4 h.

| Example | Benzene | Chlorobenzene | 1,2-Dichlorobenzene | 1,3 Dichlorobenzene | 1,4-Dichlorobenzene | 1,2,3-Trichlorobenzene | 1,2,4-Trichlorobenzene | Weight g | Weight as % of initial |
|---|---|---|---|---|---|---|---|---|---|
| 10 | 84.44% | 13.64% | 1.30% | 0.40% | 0.22% | — | — | 29.33 | 97.77 |
| 11 | 94.05% | 5.95% | — | — | — | — | — | 29.00 | 96.67 |
| 12 | 93.99% | 6.02% | — | — | — | — | — | 28.30 | 94.33 |

TABLE 7-continued

| Example | Composition and weight of the condensate of Examples 10-13 for the trial period 2-4 h. | | | | | | | Weight g | Weight as % of initial |
|---|---|---|---|---|---|---|---|---|---|
| | Benzene | Chlorobenzene | 1,2-Dichlorobenzene | 1,3 Dichlorobenzene | 1,4-Dichlorobenzene | 1,2,3-Trichlorobenzene | 1,2,4-Trichlorobenzene | | |
| 13 | 4.42% | 75.79% | 2.32% | 12.67% | 4.56% | 0.06% | 0.18% | 25.70 | 85.67 |

TABLE 8

| Example | Composition and weight of the condensate of Examples 10-13 for the trial period 4-7 h (end of the post-run time). | | | | | | | Weight g | Weight as % of initial |
|---|---|---|---|---|---|---|---|---|---|
| | Benzene | Chlorobenzene | 1,2-Dichlorobenzene | 1,3 Dichlorobenzene | 1,4-Dichlorobenzene | 1,2,3-Trichlorobenzene | 1,2,4-Trichlorobenzene | | |
| 10 | 83.50% | 10.98% | 4.33% | 0.65% | 0.37% | — | 0.17% | 30.83 | 102.78 |
| 11 | 94.37% | 5.63% | — | — | — | — | — | 28.90 | 93.00 |
| 12 | 94.02% | 5.92% | 0.06% | — | — | — | — | 27.50 | 91.67 |
| 13 | 2.44% | 81.84% | 1.89% | 9.67% | 3.56% | 0.08% | 0.88% | 33.05 | 110.17 |

Example 14

The process of Example 8 was repeated, except that instead of the mixture used there of 13.5 g of 1,2,4-trichlorobenzene and 76.5 g of benzene, a mixture of 18.00 g of 1,3,5-tribromobenzene and 72.00 g of benzene were passed over the catalyst.
Trial conditions: 150 ml of catalyst Ru/Ag-2 (Example 4) flow time 6 h, post-run time: 1 h, temperature: 400° C.
Composition 0-2 h: 90.51% benzene, 5.81% chlorobenzene, 3.68% bromobenzene;
weight: 27.63 g, 92.1% of initial.
Composition 2-4 h: 89.23% benzene, 0.43% chlorobenzene, 10.34% bromobenzene;
weight: 28.34 g 94.47% of initial.
Composition 4-7 h: 89.71% benzene, 10.22% bromobenzene, 0.07% 1,3-dibromobenzene;
weight: 28.61 g, 95.37% of initial.

Example 15

The process of Example 7 was repeated, except that instead of 400° C. a reaction temperature of 350° C. was used. The result is to be found in Tables 9-12.

Example 16

The process of Example 7 was repeated, except that instead of 400° C. a reaction temperature of 450° C. was used. The result is to be found in Tables 9-12.

TABLE 9

| | Trial conditions of Examples 15-16. Result of Trials 15 and 16 in Tables 9-12 | | | | | |
|---|---|---|---|---|---|---|
| Example | Catalyst | Catalyst amount | Starting materials | Flow time | Post-heating time | Temperature |
| 15 | Ru/Ag-1 from Example 3 | 150 ml | 13.5 g 1,2,4-trichlorobenzene + 76.5 g benzene | 6 h | 1 h | 350° C. |
| 16 | Ru/Ag-1 from Example 3 | 150 ml | 13.5 g 1,2,4-trichlorobenzene + 76.5 g benzene | 6 h | 1 h | 450° C. |

TABLE 10

| Example | Composition and weight of the condensate of Examples 15-16 for the trial period 0-2 h. | | | | | | | Weight g | Weight as % of initial |
|---|---|---|---|---|---|---|---|---|---|
| | Benzene | Chlorobenzene | 1,2-Dichlorobenzene | 1,3 Dichlorobenzene | 1,4-Dichlorobenzene | 1,2,3-Trichlorobenzene | 1,2,4-Trichlorobenzene | | |
| 15 | 88.36% | 11.64% | — | — | — | — | — | 26.67 | 88.90 |
| 16 | 91.32% | 8.68% | — | — | — | — | — | 25.80 | 86.00 |

TABLE 11

| Example | Composition and weight of the condensate of Examples 15-16 for the trial period 2-4 h. | | | | | | | Weight g | Weight as % of initial |
|---|---|---|---|---|---|---|---|---|---|
| | Benzene | Chlorobenzene | 1,2-Dichlorobenzene | 1,3 Dichlorobenzene | 1,4-Dichlorobenzene | 1,2,3-Trichlorobenzene | 1,2,4-Trichlorobenzene | | |
| 15 | 84.73% | 13.79% | 1.24 | 0.19 | 0.05 | — | — | 28.86 | 96.20 |
| 16 | 93.38% | 6.62% | — | — | — | — | — | 25.73 | 86.77 |

TABLE 12

| Example | Composition and weight of the condensate of Examples 15-16 for the trial period 4-7 h (end of the post-run time). | | | | | | | Weight g | Weight as % of initial |
|---|---|---|---|---|---|---|---|---|---|
| | Benzene | Chlorobenzene | 1,2-Dichlorobenzene | 1,3 Dichlorobenzene | 1,4-Dichlorobenzene | 1,2,3-Trichlorobenzene | 1,2,4-Trichlorobenzene | | |
| 15 | 82.07% | 11.24% | 4.91 | 0.98 | 0.80 | — | — | 29.50 | 98.33 |
| 16 | 93.12% | 5.62% | 0.62 | 0.22 | 0.22 | — | — | 26.47 | 88.23 |

What is claimed is:

1. In a process for reacting polyhalogenated aromatic compounds with monohalogenated or nonhalogenated aromatic compounds, in which the halogen of the polyhalogenated aromatic compounds is transferred to the monohalogenated or nonhalogenated aromatic compounds and the hydrogen of the monohalogenated or nonhalogenated aromatic compounds is simultaneously transferred to the polyhalogenated aromatic compounds in the presence of a catalyst, the improvement which comprises using a catalyst which contains ruthenium as the element or in the form of a compound.

2. The process of claim 1, in which the catalyst additionally contains one or more metals or compounds of metals from subgroups I and II of the Periodic Table.

3. The process of claim 1, in which the polyhalogenated aromatic compound used is di- to hexa-halogenated benzene, di- to octahlaogenated naphthalene or di- to decahalogenated biphenyl, where halogen is chlorine, bromine or iodine.

4. The process of claim 1, in which the monohalogenated or nonhalogenated aromatic compound used is fluorobenzene, chlorobenzene, bromobenzene, iodobenzene or benzene.

5. The process of claim 1, in which the catalyst used is an activated charcoal charged with ruthenium compounds.

6. The process of claim 4, in which the ruthenium compound used is ruthenium chloride.

7. The process of claim 1, in which the catalyst used is an activated charcoal charged with ruthenium compounds and additionally with compounds from subgroups I and II of the Periodic Table.

8. The process of claim 2, in which the compounds from subgroups I and II are selected from compounds of copper, silver and zinc.

9. The process of claim 1, in which the catalyst used is an activated charcoal charged with ruthenium chloride and a silver compound.

10. The process of claim 1, in which the catalyst used is an activated charcoal charged with ruthenium chloride and a copper compound.

11. The process of claim 1, in which a temperature of 200° C. to 600° C. is employed.

* * * * *

UNITED STATES PATENT AND TRADEMARK OFFICE
CERTIFICATE OF CORRECTION

PATENT NO. : 5,157,170

DATED : October 20, 1992

INVENTOR(S) : Franz-Josef Mais, et al.

It is certified that error appears in the above-identified patent and that said Letters Patent is hereby corrected as shown below:

Column 11, line 14     Delete "octahlaogenated" and substitute -- octahalogenated --

Signed and Sealed this

Third Day of May, 1994

Attest:

BRUCE LEHMAN

*Attesting Officer*     *Commissioner of Patents and Trademarks*